US009442078B2

(12) United States Patent
Hagmann

(10) Patent No.: US 9,442,078 B2
(45) Date of Patent: Sep. 13, 2016

(54) SCANNING FREQUENCY COMB MICROSCOPY (SFCM) FOR CARRIER PROFILING IN SEMICONDUCTORS

(71) Applicant: Mark J. Hagmann, Salt Lake City, UT (US)

(72) Inventor: Mark J. Hagmann, Salt Lake City, UT (US)

(*) Notice: Subject to any disclaimer, the term of this patent is extended or adjusted under 35 U.S.C. 154(b) by 1 day.

(21) Appl. No.: 14/635,828

(22) Filed: Mar. 2, 2015

(65) Prior Publication Data

US 2015/0247809 A1  Sep. 3, 2015

Related U.S. Application Data

(60) Provisional application No. 61/946,403, filed on Feb. 28, 2014.

(51) Int. Cl.
*G01N 22/00* (2006.01)
*G01Q 60/14* (2010.01)
*G01Q 60/10* (2010.01)

(52) U.S. Cl.
CPC .............. *G01N 22/00* (2013.01); *G01Q 60/14* (2013.01)

(58) Field of Classification Search
CPC ...... G01Q 60/10; G01Q 60/12; G01Q 60/14; G01N 22/00
See application file for complete search history.

(56) References Cited

U.S. PATENT DOCUMENTS 5,581,193 A * 12/1996 Weiss ..................... B82Y 10/00
                                                     324/676
5,661,301 A * 8/1997 Weiss ..................... B82Y 35/00
                                                     250/306
6,153,872 A * 11/2000 Hagmann ............... H01J 1/304
                                                     250/207
8,601,607 B2   12/2013 Hagmann et al.

OTHER PUBLICATIONS

K.Schuegraf, M.C. Abraham, A. Brand, M Naik and R. Thakur; Semiconductor Logic Technology Innovation to Achieve Sub-10 nm Manufacturing; IEEE J. Electron Device Soc. 1; (2013); 66-75.
C.C. Williams W.P. Hough and S.A. Riston; Scanning Capacitance Microscopy on a 25 mn Scale; Appl. Phys. Lett. 55; (1989); 203-205.
C.C. Williams; Two-Dimensional Dopant Profiling by Scanning Capacitance Microscopy; Annu. Rev. Mater. Sci. 29; (1999); 471-504.
J. Hilibrand and R.D. Gold; Determination of the Impurity Distribution in Junction Diodes from Capacitance-Voltage Measurements; RCA Review. 21; (1960); 245-252.

(Continued)

*Primary Examiner* — Nicole Ippolito
*Assistant Examiner* — Sean Luck
(74) *Attorney, Agent, or Firm* — Geoffrey E. Dobbin; Dobbin IP Law P.C.

(57) ABSTRACT

A microwave frequency comb (MFC) is produced when a mode-locked ultrafast laser is focused on the tunneling junction of a scanning tunneling microscope (STM). The MFC consists of hundreds of measureable harmonics at integer multiples of the pulse repetition frequency of the laser, which are superimposed on the DC tunneling current. In Scanning Frequency Comb Microscopy (SFCM) the tip and/or sample electrode of the STM is moved vertically and laterally so that the power in the MFC may be measured at one or more locations on the surface of the sample and, from the power, carrier density, and other characteristics, of the sample may be calculated. SFCM is non-destructive of the sample. While many systems are possible to practice SFCM, a preferred apparatus is disclosed.

14 Claims, 11 Drawing Sheets

(56) References Cited

OTHER PUBLICATIONS

E. Bussmann and C.C. Williams; Sub-10 nm Lateral Spatial Resolution in Scanning Capacitance Microscopy Achieved with Solid Platinum Probes; Rev. Sci. Instrum. 75; (2004); 422-425.

P. Andrei, M. Mehta and M.J. Hagmann; Simulations of 'Atomistic' Effects in Nanoscale Dopant Profiling; Transactions of the 24th Annual SEMI Advanced Semiconductor Manufacturing Conference (ASMC), Saratoga Springs, NY; pp. 194-199; 2013.

A.K. Kambham, J. Mody, M. Gilbert, S. Koelling and W. Vandervorst; Atom-Probe for FinFET Dopant Characterization; Ultramicroscopy. 111; (2011); 535-539.

S. Qin, Z . Suo, D. Fillmore, S. Lu, Y.J. Hu and A. McTeer; Ambient-Controlled Scanning Spreading Resistance Microscopy Measurement and Modeling; Appl. Phys. Lett. 103; (2013); 262105 (3 pp).

L. Zhang, H. Tanimoto, K. Adachi and A. Nishiyama; 1-nm Spatial Resolution in Carrier Profiling of Ultrashallow Junctions by Scanning Spreading Resistance Microscopy; IEEE Electron Device Lett. 29; (2008); 799-801.

K. Arstila, T Hantschel, C. Demeulemesster, A Moussa and W. Vandervorst; Microfabricated Diamond Tip for Nanoprobing; Microelectron. Eng. 86; (2009); 1222-1225.

T. Hantschel, C. Demeulemeester, P. Eyben, V. Schulz, O. Richard, H. Bender and W. Vandervorst; Conductive Diamond Tips with Sub-Nanometer Electrical Resolution for Characterization of Nanoelectronics Device Structures; Phys. Status Solidi A 206; (2009); 2077-2081.

M.J. Hagmann, A Efimov, A.J. Talor and D.A. Yarotski; Microwave Frequency-Comb Generation in a Tunneling Junction by Intermode Mixing of Ultrafast Laser Pulses; App. Phys. Lett. 99; (2011); 011112 (3 pp).

M.J. Hagmann, A.J. Taylor and D.A. Yarotski; Observation of 200th Harmonic with Fractional Linewidth of 10-10 in a Microwave Frequency Comb Generated in a Tunneling Junction; Appl. Phys. Lett. 101; (2012); 211102 (3 pp).

M.J. Hagmann, F.S. Stenger and D.A. Yarotski; Linewidth of the Harmonics in a Microwave Frequency Comb Generated by Focusing a Mode-Locked Ultrafast Laser on a Tunneling Junction; J. Appl. Phys. 114; (2013); 223107 (6 pp).

M.J. Hagmann, S. Pandey, A. Nahata, A.J. Taylor and D.A. Yarotski; Microwave Frequency Comb Attributed to the Formation of Dipoles at the Surface of a Semiconductor by a Mode-Locked Ultrafast Laser; Appl. Phys. Lett. 101; (2012) 231102 (3 pp).

X.-C. Zhang and D.H. Auston; Optoelectronic Measurement of Semiconductor Surfaces and Interfaces with Femtosecond Optics; J. Appl. Phys. 71; (1992); 326-338.

Y. Yafet and E. Yablonovitch; Virtual Photoconductivity Due to Intense Optical Radiation Transmitted Through a Semiconductor; Phys. Rev. B 43; (1992); 12480-12489.

B.B. Hu, X.-C. Zhang and D.H. Auston; Terahertz Radiation Induced by Subband-Gap Femtosecond Optical Excitation of GaAs; Phys. Rev. Lett. 67; (1991); 2709-2712.

D. Bon Der Linde, K. Sokolowski-Tinten and J. Bialkowski; Laser-Solid Interaction in the Femtosecond Time Regime; Appl. Surf. Sci. 109; (1997); 1-10.

C. Kealhofer, S.M. Foreman, S. Gerlic and M.A. Kasevich; Ultrafast Laser-Triggered Emission from Hafnium Carbide Tips; Phys. Rev. B 86; (2012) 035405 (11 pp).

M. Kruger, M. Schenk and P. Hommelhoff; Atosecond Control of Electrons Emitted from a Nanoscale Metal Tip; Nature 475; (2011); 78-81.

H. Yanagisawa, M. Hengsberger, D. Leuenberger, M. Klockner, C. Hafner, T. Gerber and J. Osterwalder; Energy Distribution Curves of Ultrafast Laser-Induced field Emission and their Implications for Electron Dynamics; Phys. Rev. Lett. 107; (2011); 087601 (5 pp).

H. Yanagisawa, C. Hafner, P. Dona, M. Klockner, D. Leuenberger, T. Greber, H. Hengsberger and J. Osterwalder; Optical Control of Field Emission Sites by Femtosecond Laser Pulses; Phys. Rev. Lett. 103:25; (2009); 257603 (4 pp).

C. Ropers, D.R. Solli, C.P. Schultz, C. Lienau and T. Elsaesser; Localized Multiphoton Emission of Femtosecond Electron Pulses from Metal Nanotips; Phys. Rev. Lett. 98:4; (2007); 043907 (4 pp).

P. Hommelhoff, C. Kealhofer and M.A. Kasevich; Ultrafast Electron Pulses from a Tungsten Tip Triggered by Low-Power Femtosecond Laser Pulses; Phys. Rev. Lett. 97:24; (2006); 247402 (4 pp).

L.D. Bell, W.J. Kaiser, M.H. Hecht and F.J. Grunthaner; Direct Control and Characterization of a Schottky Barrier by Scanning Tunneling Microscopy; Appl Phys. Lett. 52; (1988); 278-280.

R.M. Feenstra; Scanning Tunneling Spectroscopy; Surf. Sci. 299/300; (1994); 165-979.

M.J. Hagmann, Petru Andrei, Shashank Pandey and Ajay Nahata; Possible Applications of Scanning Frequency Comb Microscopy for Carrier Profiling in Semiconductors; J. Vac. Sci. Technologies B 33(2); Mar./Apr. 2015; 02B109-1-02B109-6; American Vacuum Society.

* cited by examiner

SCANNING FREQUENCY COMB MICROSCOPY (SFCM) FOR CARRIER PROFILING IN SEMICONDUCTORS

CROSS-REFERENCES TO RELATED APPLICATIONS

This Application claims priority as a non-provisional perfection of prior filed application No. 61/946,403, filed Feb. 28, 2014, and incorporates the same by reference herein in its entirety.

FIELD OF THE INVENTION

The present invention relates to the field of semiconductors and more particularly relates to a method by which carrier density may be profiled in a semiconductor using a microwave frequency comb.

BACKGROUND OF THE INVENTION

As the semiconductor industry moves from its fifth to sixth decade, the continued advancement in agreement with Moore's Law causes many challenges as the lithography enters the sub-10 nm regime (K. Schuegraf, M. C. Abraham, A. Brand, M. Naik and R. Thakur, "Semiconductor logic technology innovation to achieve sub-10 nm manufacturing," IEEE J. Electron Device Soc. 1 (2013) 66-75). One major need, which is listed in the roadmaps for the industry, is new means of metrology to provide much greater resolution in profiling the concentration of dopants and carriers. At sub-10 nm lithography the mean spacing for nearest neighbors of the dopant atoms is comparable with the size of each transistor or other components in an integrated circuit. This finer lithography essentially makes a measured average dopant atom concentration insufficient for metrology. Thus, it is essential to distinguish between profiling of the discrete dopant atoms which are at fixed positions and profiling of the mobile carriers which may be considered to be continuous distribution throughout a volume.

Scanning capacitance microscopy (SCM) was introduced in 1989 and this method is still widely used in the semiconductor industry for carrier profiling (C. C. Williams, W. P. Hough and S. A Riston, "Scanning capacitance microscopy on a 25 nm scale," Appl. Phys. Lett. 55 (1989) 203-205). In SCM, the surface of a semiconductor is coated with a thin layer of oxide and a metal tip is scanned across the surface while in contact with the oxide (C. C. Williams, "Two-dimensional dopant profiling by scanning capacitance microscopy," Annu. Rev. Mater. Sci. 29 (1999) 471-504). The metal tip is given a negative DC bias relative to the sample for n-type semiconductors, or a positive bias for p-type samples to cause a depletion layer, and the depletion capacitance is measured as a function of the applied bias to determine local values of the carrier concentration as an extension of how this is done in one dimension with capacitance-voltage profiling (J. Hilibrand and R. D. Gold, "Determination of the impurity distribution in junction diodes from capacitance-voltage measurements," RCA Review. 21 (1960) 245-252). In SCM the total capacitance (depletion layer plus fringing) is measured at high frequencies, typically 915 MHz, which requires a resonant circuit because the changes in the depletion capacitance are typically only 1 part per million of the total capacitance. The finest resolution ever claimed with SCM is 10 nm, and this limit is readily understood because this dimension is comparable with the radius of the metal tip (E. Bussmann and C. C. Williams, "Sub-10 nm lateral spatial resolution in scanning capacitance microscopy achieved with solid platinum probes," Rev. Sci. Instrum. 75 (2004) 422-425). However, at high resolution it is necessary for the oscillator to drive the semiconductor over the full range from accumulation through inversion to obtain a measurable output signal. Recent "atomistic" simulations confirm the observation that SCM "hits a wall" below 45 nm lithography and is not suitable for carrier profiling with 32 or 22 nm lithography (P. Andrei, M. Mehta and M. J. Hagmann, "Simulations of 'atomistic' effects in nanoscale dopant profiling," Transactions of the $24^{th}$ Annual SEMI Advanced Semiconductor Manufacturing Conference (ASMC), Saratoga Springs, N.Y., pp. 194-199, 2013).

At the present time scanning spreading resistance microscopy (SSRM) is considered to provide the finest resolution for profiling carriers in semiconductors (A. K. Kambham, J. Mody, M. Gilbert, S. Koelling and W. Vandervorst, "Atom-probe for FinFET dopant characterization," Ultramicroscopy. 111 (2011) 535-539; 5. Qin, Z. Suo, D. Fillmore, S. Lu, Y. J. Hu and A. McTeer, "Ambient-controlled scanning spreading resistance microscopy measurement and modeling," Appl. Phys. Lett. 103 (2013) 262105 (3 pp.)). In SSRM the electrical resistance is measured between a sharp conductive probe tip and a large current-collecting back electrode as the probe is inserted into the semiconductor at various points on the surface. When the downward force applied to the probe exceeds a certain threshold, to penetrate the native oxide coating and establish a stable contact, the measured resistance is dominated by the spreading resistance. Diamond is frequently used for the probe tip because of its extreme hardness and high Young's modulus, with electrical conductivity caused by doping. Carrier profiling with a resolution of 1 or 2 nm has been claimed using SSRM but it is unlikely that much finer resolution can be obtained because of the limited strength of materials for the probe tips (L. Zhang, H. Tanimoto, K. Adachi and A. Nishlyama, "1-nm spatial resolution in carrier profiling of ultrashallow junctions by scanning spreading resistance microscopy," IEEE Electron Device Lett. 29 (2008) 799-801; K. Arstila, T. Hantschel, C. Demeulemeester, A. Moussa and W. Vandervorst, "Microfabricated diamond tip for nanoprobing," Microelectron. Eng. 86 (2009) 1222-1225; T. Hantschel, C. Demeulemeester, P. Eyben, V. Schulz, O. Richard, H. Bender and W. Vandervorst, "Conductive diamond tips with sub-nanometer electrical resolution for characterization of nanoelectronics device structures," Phys. Status Solidi A 206 (2009) 2077-2081). Also, SSRM is a destructive process because the surface of the semiconductor is changed by inserting the probe tips, so it is not possible to repeat the measurements at a given location on a sample. It should also be noted that while tips with a radius of only 1 or 2 nm may be fabricated, this dimension is the size of the disruption of the lattice of the semiconductor so the true resolution must be larger than this. As the inserted probe redistributes sample matter, SSRM is also limited in that adjacent insertion points cannot be so close together as to measure resistance at a disturbed locus (from redistribution) or one where the structural integrity has degraded (from the hole left over from the previous test). Also, since the probe is inserted into the semiconductor, it cannot be used in a manner to scan the surface of the semiconductor sample as it cannot move seamlessly across that surface.

The present invention is a method of using a microwave frequency comb to measure microwave attenuation across a volume of a sample in order to determine spreading resistance. When a mode-locked ultrafast laser is focused on the tunneling junction of a scanning tunneling microscope (STM) with a metallic sample, a microwave frequency comb (MFC) is superimposed on the DC tunneling current (M. J. Hagmann, A. Efimov, A J. Talor and D. A. Yarotski, "Microwave frequency-comb generation in a tunneling junction by intermode mixing of ultrafast laser pulses," App. Phys. Lett. 99 (2011) 011112 (3 pp)). The MFC, which is caused by optical rectification, contains hundreds of measurable harmonics at integer multiples of the pulse repetition frequency of the laser, setting the present state-of-the-art for narrow linewidth at microwave frequencies (M. J. Hagmann, A. J. Taylor and D. A. Yarotski, "Observation of 200$^{th}$ harmonic with fractional linewidth of $10^{-10}$ in a microwave frequency comb generated in a tunneling junction," Appl. Phys. Lett. 101 (2012) 241102 (3 pp); M. J. Hagmann, F. S. Stenger and D. A. Yarotski, "Linewidth of the harmonics in a microwave frequency comb generated by focusing a mode-locked ultrafast laser on a tunneling junction," J. Appl. Phys. 114 (2013) 223107 (6 pp)).

When using silicon samples in a STM, a MFC at harmonics of the pulse repetition frequency of a Ti:sapphire mode-locked ultrafast laser, independent of whether or not there is a DC tunneling current is seen (M. J. Hagmann, S. Pandey, A. Nahata, A. J. Taylor and D. A. Yarotski, "Microwave frequency comb attributed to the formation of dipoles at the surface of a semiconductor by a mode-locked ultrafast laser," Appl. Phys. Lett. 101 (2012) 231102 (3 pp)). However, when using SiC or other semiconductors in which the band-gap energy exceeds the photon energy of the laser, there is no frequency comb without a DC tunneling current. This may be understood in that, when the photon energy exceeds the band-gap energy, the laser creates electron-hole pairs in the semiconductor and the motion of these particles causes surge currents at the harmonics. Others have measured terahertz radiation generated by the surge currents, noting that this only occurs when the photon energy exceeds the band-gap energy, but they did not measure the surge currents or appreciate that the terahertz radiation has the structure of a frequency comb (X. C. Zhang and D. H. Auston, "Optoelectronic measurement of semiconductor surfaces and interfaces with femtosecond optics," J. Appl. Phys. 71 (1992) 326-338).

A laser with photon energy somewhat less than the band-gap energy may cause the electron and hole wave functions to penetrate into the classically forbidden gap to cause "virtual photoconductivity" in what is called the "Inverse Franz-Keldysh effect" (Y. Yafet and E. Yablonovitch, "virtual photoconductivity due to intense optical radiation transmitted through a semiconductor," Phys. Rev. B 43 (1991) 12480-12489). Terahertz radiation has been generated with this effect by creating virtual carriers with intense femtosecond laser pulses even though the photon energy is less than the band-gap energy of the semiconductor (B. B. Hu, X. C. Zhang and D. H. Auston, "terahertz radiation induced by subband-gap femtosecond optical excitation of GaAs," Phys. Rev. Lett. 67 (1991) 2709-2712). To summarize, when using lasers with a photon energy less than the band-gap energy of a semiconductor, and moderate values of the power flux density, typically below $10^{13}$ W/m$^2$, only the MFC which is caused by optical rectification is seen.

The sequence of four steps in the interaction of the radiation from a femtosecond laser with solids, including semiconductors, has been listed as follows (D. von der Linde, K. Sokolowski-Tinten and J. Bialkowski, "Laser-solid interaction in the femtosecond time regime," Appl. Surf. Sci. 109 (1997) 1-10):

(1) Primary process: Electrons are excited from their equilibrium states by the absorption of photons, for example, by the creation of electron-hole pairs in a semiconductor when the photon energy is greater than the band-gap energy. The probability of multiphoton processes is more likely with increased laser intensity. The primary process of electronic excitation is associated with a very short-lived coherent polarization of the material having a time scale of about 10 fs.

(2) Dephasing and quasi-equilibrium: There is a complex of secondary processes having different time scales. First dephasing of the polarization of the material occurs at approximately 10 fs. Then the initial distribution of the excited electronic states is rapidly changed by carrier-carrier interaction processes, and quasi-equilibrium is established among the electrons on a time scale of about 100 fs so that the energy distribution of the carriers is described by the Fermi Dirac distribution having an electron temperature that is greater than the lattice temperature.

(3) Cool down by the emission of phonons: The electron temperature of the quasi-equilibrium electrons cools down by the emission of phonons over a time scale of 100 to 1000 fs. These phonons relax predominantly by inharmonic interaction with other phonon modes.

(4) Redistribution of the phonons: The final stage of the thermalization process is the redistribution of the phonons over the entire Brillouin zone according to a Bose-Einstein distribution. At this point the temperature of the laser-excited material can be defined, and the energy distribution is characterized by the temperature. The time scale for this process is typically several picoseconds, and it is followed by thermal diffusion on a time scale of the order of 10 ps.

Several groups have used mode-locked Ti:sapphire lasers to generate femtosecond pulses of electrons (C. Kealhofer, S. M. Foreman, S. Gerlich and M. A. Kasevich, "Ultrafast laser-triggered emission from hafnium carbide tips," Phys. Rev. B 86 (2012) 035405 (11 pp); M. Kruger, M. Schenk and P. Hommelhoff, "Atosecond control of electrons emitted from a nanoscale metal tip," Nature 475 (2011) 78-81; H. Yanagisawa, M. Hengsberger, D. Leuenberger, M. Kiockner, C. Hafner, T. Gerber and J. Osterwalder, "Energy distribution curves of ultrafast laser-induced field emission and their implications for electron dynamics," Phys. Rev. Lett. 107 (2011) 087601 (5 pp); H. Yanagisawa, C. Hafner, P. Dona, M. Klockner, D. Leuenberger, T. Greber, M. Hengsberger and J. Osterwalder, "Optical control of field-emission sites by femtosecond laser pulses," Phys. Rev. Lett. 103:25 (2009) 257603 (4 pp); C. Ropers, D. R. Solli, C. P. Schultz, C. Lienau and T. Elsaesser, "Localized multiphoton emission of femtosecond electron pulses from metal nanotips," Phys. Rev. Lett. 98:4 (2007) 043907 (4 pp); P. Hommelhoff, C. Kealhofer and M. A. Kasevich, "Ultrafast electron pulses from a tungsten tip triggered by low-power femtosecond laser pulses," Phys. Rev. Lett. 97:24 (2006) 247402 (4 pp). Since the center wavelength of 800 nm is not sufficient to cause photoemission with a single photon, the electron emission can only be caused by one or more of the following four processes (C. Kealhofer, S. M. Foreman, S. Gerlich and M. A. Kasevich, "Ultrafast laser-triggered emission from hafnium carbide tips," Phys. Rev. B 86 (2012) 035405 (11 pp):

(1) Multi-photon emission: When the energy of a single photon is less than the work function of the tip electrode, a number N of photons can liberate an electron across the barrier. For example, multi-photon emission has been observed with N=3 for tungsten and N=4 for gold.

(2) Photo-assisted field emission: When a DC bias is applied to cause field emission, one or more photons can raise the energy of an electron above the Fermi level to increase the probability of barrier penetration in order to increase the emitted current.

(3) Above-threshold photoemission: As the intensity of the optical field is increased, multi-photon processes may occur having higher values of N than the minimum which is required for multi-photon emission.

(4) Transient thermally-enhanced field emission: When a DC bias is applied to cause field emission, heating the tip electrode changes the distribution of energy for the electrons which increases the current. Thus, depending on the heat transfer at the apex of the tip electrode, it is possible for a laser to cause changes in the emitted current at time scales on the order of picoseconds.

Typically the laser pulse has a duration of 15 fs and the pulse repetition frequency is 74.254 MHz, so the spacing between consecutive pulses is approximately 13 ns (M. J. Hagmann, A. Efimov, A. J. Talor and D. A. Yarotski, "Microwave frequency-comb generation in a tunneling junction by intermode mixing of ultrafast laser pulses," App. Phys. Lett. 99 (2011) 011112 (3 pp); M. J. Hagmann, A. J. Taylor and D. A. Yarotski, "Observation of 200th harmonic with fractional linewidth of $10^{-10}$ in a microwave frequency comb generated in a tunneling junction," Appl. Phys. Lett. 101 (2012) 241102 (3 pp); M. J. Hagmann, F. S. Stenger and D. A. Yarotski, "Linewidth of the harmonics in a microwave frequency comb generated by focusing a mode-locked ultrafast laser on a tunneling junction," J. Appl. Phys. 114 (2013) 223107 (6 pp). In SFCM, only the use of the laser in a scanning tunneling microscope (STM) with a semiconductor band-gap energy that exceeds the photon energy of the laser is considered. Furthermore, only moderate laser intensity is considered, so that by analogy to the case of laser assisted field emission, the primary process of the four interaction steps can only be photo-assisted tunneling, in which the electrons are raised above the Fermi level to increase the probability of tunneling. The slower processes which take place after each laser pulse are completed before the following pulse, so that it appears that they would have no effect on measurements of the microwave frequency comb.

Interaction of Laser Radiation with a Tunneling Junction at the Surface of a Semiconductor Previous analyses have considered the use of a metal sample in a STM and approximated the current-voltage (I-V) relationship as a cubic polynomial (M. J. Hagmann, A. Efimov, A. J. Talor and D. A. Yarotski, "Microwave frequency-comb generation in a tunneling junction by intermode mixing of ultrafast laser pulses," App. Phys. Lett. 99 (2011) 011112 (3 pp); M. J. Hagmann, F. S. Stenger and D. A. Yarotski, "Linewidth of the harmonics in a microwave frequency comb generated by focusing a mode-locked ultrafast laser on a tunneling junction," J. Appl. Phys. 114 (2013) 223107 (6 pp). However, the I-V relationship is more complicated with semiconductor samples, as described in the studies of scanning tunneling spectroscopy (STS) (L. D. Bell, W. J. Kaiser, M. H. Hecht and F. J. Grunthaner, "Direct control and characterization of a Schottky barrier by scanning tunneling microscopy," Appl. Phys. Lett. 52 (1988) 278-280; (R. M. Feenstra, "Scanning tunneling spectroscopy," Surf. Sci. 299/300 (1994) 965-979). FIG. 1 from Feenstra, et al. shows the I-V curves for n- and p-type silicon with five I-V curves that were obtained using different tip-sample separations, as well as the corresponding MIS energy-band diagram (lower right inset). The five I-V curves labeled a-e were obtained with the p-type sample using five different tip-sample separations under feedback control with a tunnel current of 1 nA and sample voltages of 01, 0.2, 0.4, and 0.5 V for the spectra labeled a-e, respectively. In each case the DC tunneling current is shown as a function of the sample voltage with the tip electrode at zero potential. The reduced current shown at negative sample potentials in the five curves at the central part of the figure may be explained by the formation of a depletion layer at the surface of the semiconductor. Note that the set of five curves shows the effects of distortion caused by increasing the tip-sample distance which may be understood in that this effectively averages the results over a wider area of the sample.

Because of the more complicated I-V relationship when using a semiconductor sample it is noted that the DC tunneling current with no laser, $I_0$, is a function of the applied DC potential $V_0$, where the other parameters including the tip-sample separation are held constant. When the radiation from a mode-locked ultrafast laser is focused on a tunneling junction, the electric field of the radiation effectively superimposes a time-varying potential on the applied DC bias because the tunneling junction is much smaller than the wavelength. Thus, assuming that each laser pulse is Gaussian, and neglecting the effects of the finite duration of the pulse train, the total effective potential across the tunneling junction is given by $$V(t) = V_0 + \sum_{n=-\infty}^{\infty} V_n e^{-\left(\frac{t-nT}{\tau}\right)^2} \cos[\omega_0(t-nT) + \phi] \quad (1)$$

A Maclaurin series may be used to give the following expression for the total current I(t) as a function of the total potential:

$$I(t) = I_0 + \left(\frac{dI}{dV}\right)_{V=V_0} \sum_{n=-\infty}^{\infty} e^{-\left(\frac{t-nT}{\tau}\right)^2} \cos[\omega_0(t-nT) + \phi] + \frac{1}{2}\left(\frac{dI}{dV}\right)^2_{V=V_0} \left(\sum_{n=-\infty}^{\infty} e^{-\left(\frac{t-nT}{\tau}\right)^2} \cos[\omega_0(t-nT) + \phi]\right)^2 + \ldots \quad (2)$$

The cross terms in the square of the second summation in Eq. (2) may be neglected because $T \gg \tau$, to give Eq. (3), and a trigonometric identity is used to obtain Eq. (4).

$$I(t) = I_0 + \left(\frac{dI}{dV}\right)_{V=V_0} \sum_{n=-\infty}^{\infty} V_n e^{-\left(\frac{t-nT}{\tau}\right)^2} \cos[\omega_0(t-nT) + \phi] + \frac{1}{2}\left(\frac{dI}{dV}\right)^2_{V=V_0} \sum_{n=-\infty}^{\infty} V_n^2 e^{-2\left(\frac{t-nT}{\tau}\right)^2} \cos^2[\omega_0(t-nT) + \phi] + \ldots \quad (3)$$

$$I(t) = I_0 + \frac{1}{4}\left(\frac{dI}{dV}\right)^2_{V=V_0} \sum_{n=-\infty}^{\infty} V_n^2 e^{-2\left(\frac{t-nT}{\tau}\right)^2} + \left(\frac{dI}{dV}\right)_{V=V_0} \sum_{n=-\infty}^{\infty} V_n e^{-\left(\frac{t-nT}{\tau}\right)^2} \cos[\omega_0(t-nT) + \phi] + \frac{1}{4}\left(\frac{dI}{dV}\right)^2_{V=V_0} \sum_{n=-\infty}^{\infty} V_n^2 e^{-2\left(\frac{t-nT}{\tau}\right)^2} \cos[2\omega_0(t-nT) + \phi] + \ldots \quad (4)$$

Neglecting terms beyond second order in the Maclaurin series, deleting all terms at the optical frequency and its harmonics, and neglecting amplitude noise as well as phase jitter, yields the following expression for the signal that is generated by optical rectification:

$$I(t) = I_0 + \frac{1}{4}\left(\frac{dI}{dV}\right)^2_{V=V_0} V_1^2 \sum_{n=-\infty}^{\infty} e^{-2\left(\frac{t-nT}{\tau}\right)^2} \quad (5)$$

Because ideal periodicity is assumed, a Fourier series may be used to represent the second term in the time-dependent tunneling current. A single pulse is centered at time t=0 to form an even series, and again requires that $\tau \ll T$ so that there is no significant overlap from adjacent pulses.

$$f(t) \equiv \sum_{n=-\infty}^{\infty} e^{-2\left(\frac{t-nT}{\tau}\right)^2} = \frac{a_0}{2} + \sum_{m=1}^{\infty} a_m \cos\left(\frac{2m\pi t}{T}\right) \quad (6A)$$

where $$a_0 = \frac{4}{T}\int_0^{\frac{T}{2}} f(t)dt \quad (6B)$$

$$a_m = \frac{4}{T}\int_0^{\frac{T}{2}} f(t)\cos\left(\frac{2m\pi t}{T}\right)dt \quad (6C)$$

Solving for the coefficients:

$$a_m = \frac{4}{T}\int_0^{\frac{T}{2}} e^{-2\left(\frac{t-nT}{\tau}\right)^2} \cos\left(\frac{2m\pi t}{T}\right)dt \quad (7A)$$

$$a_m = \frac{4}{T}\int_0^{\infty} e^{-2\left(\frac{t-nT}{\tau}\right)^2} \cos\left(\frac{2m\pi t}{T}\right)dt \quad (7B)$$

$$a_m = \frac{4}{T}\int_0^{\infty} e^{-2\left(\frac{t}{\tau}\right)^2} \cos\left(\frac{2m\pi t}{T}\right)dt \quad (7C)$$

$$a_m = \sqrt{2\pi}\left(\frac{\tau}{T}\right)e^{-\frac{m^2\pi^2}{2}\left(\frac{\tau}{T}\right)^2} \quad (7D)$$

$$f(t) \equiv \sum_{n=-\infty}^{\infty} e^{-2\left(\frac{t-nT}{\tau}\right)^2} = \quad (8)$$

$$\sqrt{\frac{\pi}{2}}\left(\frac{\tau}{T}\right) + \sqrt{2\pi}\left(\frac{\tau}{T}\right)\sum_{n=-\infty}^{\infty} e^{-\frac{m^2\pi^2}{2}\left(\frac{\tau}{T}\right)^2} \cos\left(\frac{2m\pi t}{T}\right)$$

Thus, the total tunneling current may be written as follows, where the DC terms are grouped within brackets to separate them from the sinusoidal terms:

$$I(t) = \left[I_0 + \frac{\sqrt{2\pi}}{8}\left(\frac{dI}{dV}\right)^2_{V=V_0}\left(\frac{\tau}{T}\right)V_1^2\right] + \quad (9)$$

$$\frac{\sqrt{2\pi}}{4}\left(\frac{dI}{dV}\right)^2_{V=V_0}\left(\frac{\tau}{T}\right)V_1^2 \sum_{n=-\infty}^{\infty} e^{-\frac{m^2n^2}{2}\left(\frac{\tau}{T}\right)^2} \cos\left(\frac{2m\pi t}{T}\right)$$

Equation (9) shows that the process of optical rectification superimposes a MFC with a DC offset on the tunneling current which would be present without the laser.

Means for Carrier Profiling by SFCM that Require a Depletion Region in the Semiconductor U.S. Pat. No. 8,601,607 specifically describes the creation and the use of a MFC for dopant profiling in which a depletion region is formed within the semiconductor and the power at the harmonics is measured with a spectrum analyzer. The intention of forming a depletion region was to create a small volume of the semiconductor having electrical properties that are significantly different from those of the rest of the semiconductor to cause a high series impedance that measurably increases the attenuation of the MFC. Thus, the average properties would be determined in a volume that may be adjusted in size by varying the DC bias, and scanned across the semiconductor by moving the tip or the sample.

A full understanding of carrier profiling by SFCM would require consistent numerical quantum simulations, but approximate analytical solutions with several equivalent circuit models can illustrate the principles. In particular, it is necessary to carefully model the capacitance of the depletion layer which is done for the first time in this disclosure.

FIG. 2 is a block diagram for the apparatus that may be used to measure the MFC with a semiconductor sample, for which the DC and high-frequency equivalent circuits are shown in FIGS. 3A and 3B, respectively. The two equivalent circuits assume an ideal Bias-T, which could be placed in either the tip or sample circuit. The bulk resistance $R_B$ represents the resistance of the bulk region of the semiconductor, but may include other elements of the series circuit. While $R_D$ represents the resistance of the depletion region, at high frequencies the effective value of $R_D$ may be quite different from that at DC, and in general both $R_D$ and $C_D$ will depend on the frequency. Furthermore, appropriate effective values for $R_D$ should be used to allow for the change in the mobility of the charge carriers with various magnitudes of the DC and high-frequency electric fields.

Since optical rectification takes place within the tunneling junction, which has an impedance of at least 1 MΩ, the source for the MWFC is represented as a constant current source at each of the harmonics when the circuit that is presented to the tunneling junction has an impedance much less than this resistance. Presumably, if the impedance that is presented to the tunneling junction were much greater than the impedance of the tunneling junction (1 MΩ) the tunneling junction would act as a constant voltage source at each of the harmonics. Let $I_{Sn}$ be the complex amplitude of the current at the nth harmonic in the constant current source within the tunneling junction and $\omega_0 = 2\pi/T$ be the angular frequency at the fundamental. Then, by analysis of the high-frequency equivalent circuit, the power delivered to the spectrum analyzer at the nth harmonic is given by the following expression:

$$P_n = \frac{(1+F^2n^2)R_{SA}I_{Sn}I_{Sn}^*}{2[1+(2DE+2^2+2EF+F^2)n^2+D^2F^2n^4]} \text{ where} \quad (10A)$$

$$D = \omega_0(R_{SA}+R_B)C_S \quad (10B)$$

$$E = \omega_0 R_D C_S \quad (10C)$$

$$F = \omega_0 R_D C_D \quad (10D)$$

For the special case with no depletion layer $$P_n = \frac{R_{SA}I_{Sn}I_{Sn}^*}{2(1+D^2n^2)} = \frac{R_{SA}I_{Sn}I_{Sn}^*}{2[1+n^2\omega_0^2(R_{SA}+R_B)^2C_S^2]} \quad (11)$$

Equation (11) is consistent with measurements made using a gold sample which show that the measured microwave power varies inversely with the square of the frequency [13]. For example, using a gold sample the 200th harmonic at 14.85 GHz delivers a power of −145 dBm to the spectrum analyzer which has an impedance of 50 Ohms. Thus, for the special case where there is no semiconductor, an RMS current of 250 pA would flow into the sample at 14.85 GHz. At the nth harmonic the current would be equal to (200/n)250 pA and the frequency would be (n/200)14.85 GHz.

Others have determined well-known expressions for the depth of a depletion region as a function of the applied bias in the one-dimensional problem for a rectangular slab of semiconductor (J. Hilibrand and R. D. Gold, "Determination of the impurity distribution in junction diodes from capacitance-voltage measurements," RCA Review. 21 (1960) 245-252). Their derivation is readily extended to give the following solution for the three-dimensional problem in which a spherical electrode having radius $R_0$ is at the origin in a semiconductor have a concentration of dopant atoms N, and a potential $V_D$ is applied to cause a depletion region with radius R.

$$R\left(\left[\sqrt{K^2 - \frac{K}{4}} + K - \frac{1}{8}\right]^{\frac{1}{3}} - \left[\sqrt{K^2 - \frac{K}{4}} - K + \frac{1}{8}\right]^{\frac{1}{3}} + \frac{1}{2}\right)R_0 \quad (12A)$$

where $$K = \frac{3\varepsilon V_D}{2eNR_0^2} \quad (12B)$$

The capacitance between the outer radius of the depletion region and the spherical electrode is given by the following expression:

$$C_S = \frac{4\pi\varepsilon_r\varepsilon_0 R R_0}{R - R_0} \quad (13)$$

The significance of the difference between the two- and three-dimensional problems will be seen in the following simulations.

The following algorithm has been tested as a simple means for simulating the forward problem to examine the sensitivity to the carrier density when profiling by SFCM:
1. Specify values for $R_0$, N, $V_D$, $\varepsilon_r$ the dielectric constant of the semiconductor, $f_R$ the pulse repetition frequency of the laser, $C_S$, $T_D=R_D C_D$ which is the time constant for the depletion region, Re the resistance of the bulk layer of the semiconductor, and $R_{SA}$ the input impedance of the spectrum analyzer.
2. Use Eqs. (12A), (12B), and (13) to determine Cs, and take one-half of this value as $C_D$, corresponding to the hemisphere within the semiconductor. Then determine $R_D=T_D/C_D$ and $T_D$, or specify the value of $R_D$.
3. Calculate $I_{DC}$, the DC current in the depletion region, which is equal to the DC tunneling current, by using $I_{DC}=V_D/R_D$.
4. Assume that the current at each harmonic within the tunneling junction is proportional to $I_{DC}$.
5. Use Eqs. (10A), (10B), (10C), and (10D) to determine the power that is measured with the spectrum analyzer.

As a correction, it would be more appropriate to separate the spreading resistance $R_{SP}$ between the outer surface of the depletion region from the balance of the bulk resistance in order to allow for the effect of changes in the radius R with the applied bias.

In summary, because of the reduced effect of the applied potential on the thickness of the depletion region in the three-dimensional solution, as compared to the one-dimensional solution, the use of a depletion region does not appear to cause the density of the dopant atoms to have a significant effect on the power in the MFC.

Coulomb Explosion

With a metal sample, the increment of charge at the surface of the sample caused by each pulse of electrons in the tunneling current is rapidly dispersed as a high-frequency current. However, with a semiconductor sample the process for dispersal of this charge are more complicated. Simulations suggest that during each laser pulse an incremental charge of electrons or holes is formed which disperses rapidly due to intense electrostatic repulsion in what is called "Coulomb Explosion," followed by scattering process and then thermalization. It is preferable to forward-bias the tunneling junction to avoid forming a depletion region in order to maximize the current in the Coulomb Explosion. Coulomb Explosions are formed in many different environments such as nuclear disintegration and ionization by an intense ultrashort laser pulses (V. P. Krainov and A. S. Roshchupkin, J. Phys. B: At. Mol. Opt. Phys. 34, L297 (2001); D. Feldbaum, N. V. Morrow, S. K. Dutta, and G. Raithel, Phys. Rev. Lett. 89, 173004 (2002); L. Hong-Yu, L. Jian-Sheng W. Cheng, N. Guo-Quan, L. Ru-Xin, and X. Zhi-Zhan, Chin. Phys. B 17, 1237 (2008); A. V. Ivlev, Phys. Rev. E 87, 025102 (2013). When the semiconductor is forward-biased to maximize the tunneling current, the tunneling electrons create a dense positively charged spot with excess holes at the surface of an n-type semiconductor (G. J. de Raad, P. M. Koenraad, and J. H. Wolter, Surf. Sci. 556, 39 (2004). Conversely, a dense negatively charged spot, with excess electrons, is formed on a p-type semiconductor. Subsequently, intense electrostatic repulsion causes the charged particles to move rapidly away from the initial spot. FIG. 5 is a diagram illustrating present understanding of the processes, which describes a forward-biased tunneling junction with a semiconductor sample. This figure shows an n-type semiconductor but the polarity of the voltage source and the directions for the carriers and tunneling electrons would be reversed with a p-type semiconductor. In measurements with no laser, when the sample has a negative bias so electrons tunnel from the semiconductor to the tip (forward-biased for n-type and reverse-biased for p-type), the STM provides an image of the filled-states at the surface of the semiconductor. Conversely, when the sample has a positive bias so electrons tunnel from the tip to the semiconductor, the image shows the empty-states at the surface of the semiconductor. FIG. 5 shows the formation of a spot having excess holes that are represented by plus signs at the surface of the semiconductor. Arrows show the outward movement of the holes in the Coulomb Explosion, followed by a region in which the energy of the excess holes from the Coulomb Explosion is still dominant, which is followed by quasi-equilibrium transport.

Current pulses generated by a Coulomb Explosion dissipate rapidly and the pulse-width increases during propagation, so it is necessary to sample the pulse close to the tunneling junction before the pulse has dissipated. Ideally, this distance should be under 100 μm, but the exact distance will vary inversely with the dopant density of a semiconductor and will therefore vary depending on the semiconductor sample.

The present invention represents a departure from the prior art in that the method of the present invention allows for non-destructive measurement of the carrier density of a semi-conductive sample on the order of 1 nm or smaller, without causing a depletion region in the sample.

SUMMARY OF THE INVENTION

In view of the foregoing disadvantages inherent in the known types of carrier profiling, this invention provides a non-destructive and more precise method by which carrier density may be measured in a semiconductor sample. As such, the present invention's general purpose is to provide a new and improved method that is less complicated than the prior art, non-destructive to the sample, and provides more refined information to the user.

To accomplish these objectives, the method comprises focusing a mode-locked ultra-fast laser on a tunneling junction of an STM and applying a forward bias voltage such that no depletion region is generated in a semiconductor sample in the STM. The laser then generates a microwave frequency comb. This comb may be measured at many different frequencies such that harmonics, based on the pulse repetition rate of the laser pulses, may be analyzed. Then, analyzing the power of the MFC, and thereby determining its attenuation, provides a measurement of the spreading resistance of the sample, thereby measuring the free carrier density.

The more important features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims, reference being made to the accompanying drawings forming a part of this specification wherein like reference characters designate corresponding parts in the several views.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT

With reference now to the drawings, the preferred embodiment of the method of scanning frequency comb microscopy is herein described. It should be noted that the articles "a", "an", and "the", as used in this specification, include plural referents unless the content clearly dictates otherwise.

Figure 1:
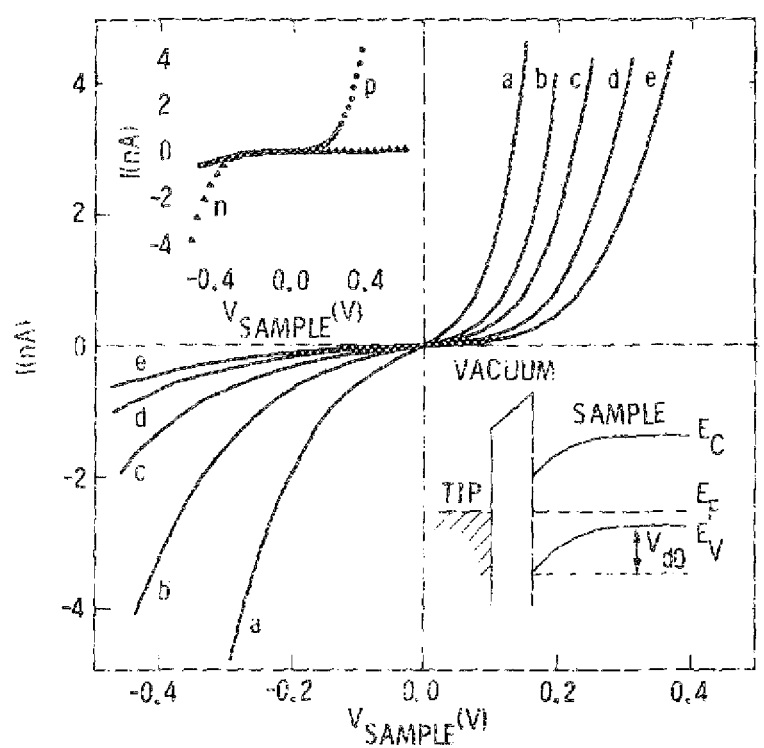
FIG. 1 is a graph showing STS I-V curves are shown in the upper left inset for both n- and p-type Si.
Figure 2:
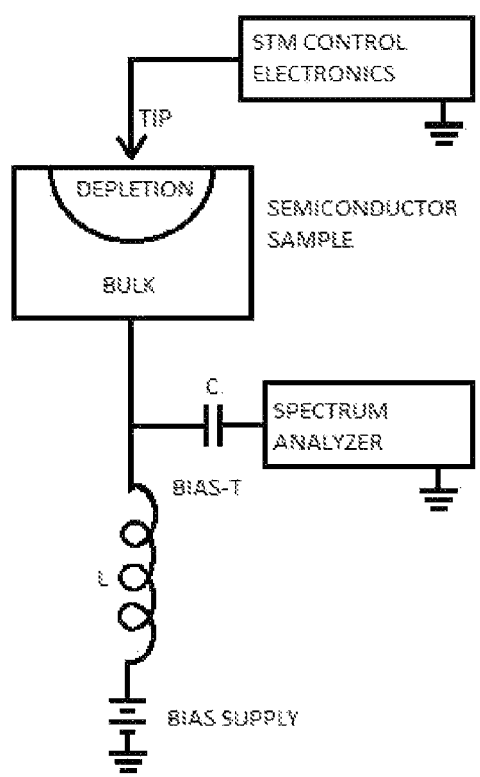
FIG. 2 is a block diagram of an apparatus used to measure the MFC with a semiconductor sample using a prior art depletion region/capacitance methodology.
Figure 3:
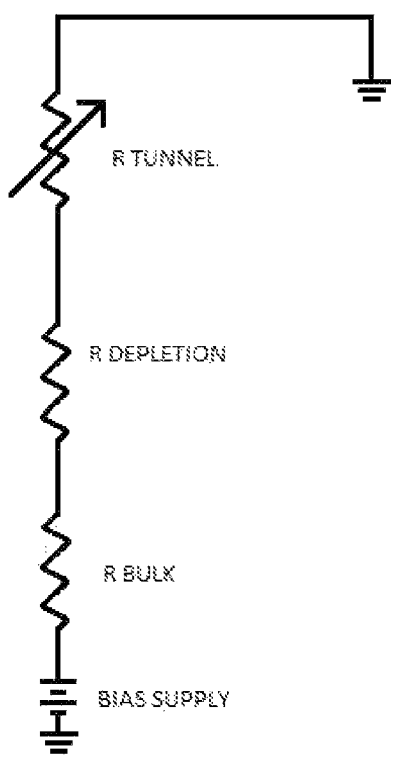
FIG. 3 is a circuit diagram depicting the DC equivalent circuit of the apparatus of FIG. 2.
Figure 4:
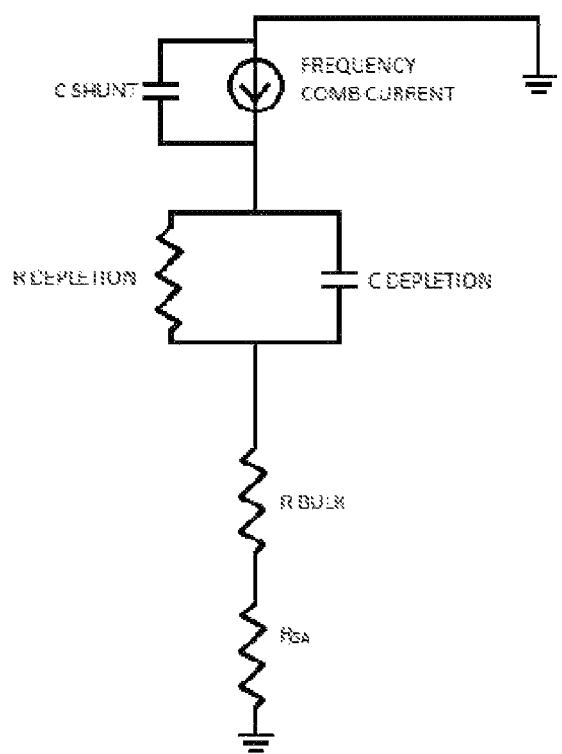
FIG. 4 is a circuit diagram depicting the high-frequency equivalent circuit of the apparatus of FIG. 2.
Figure 5:
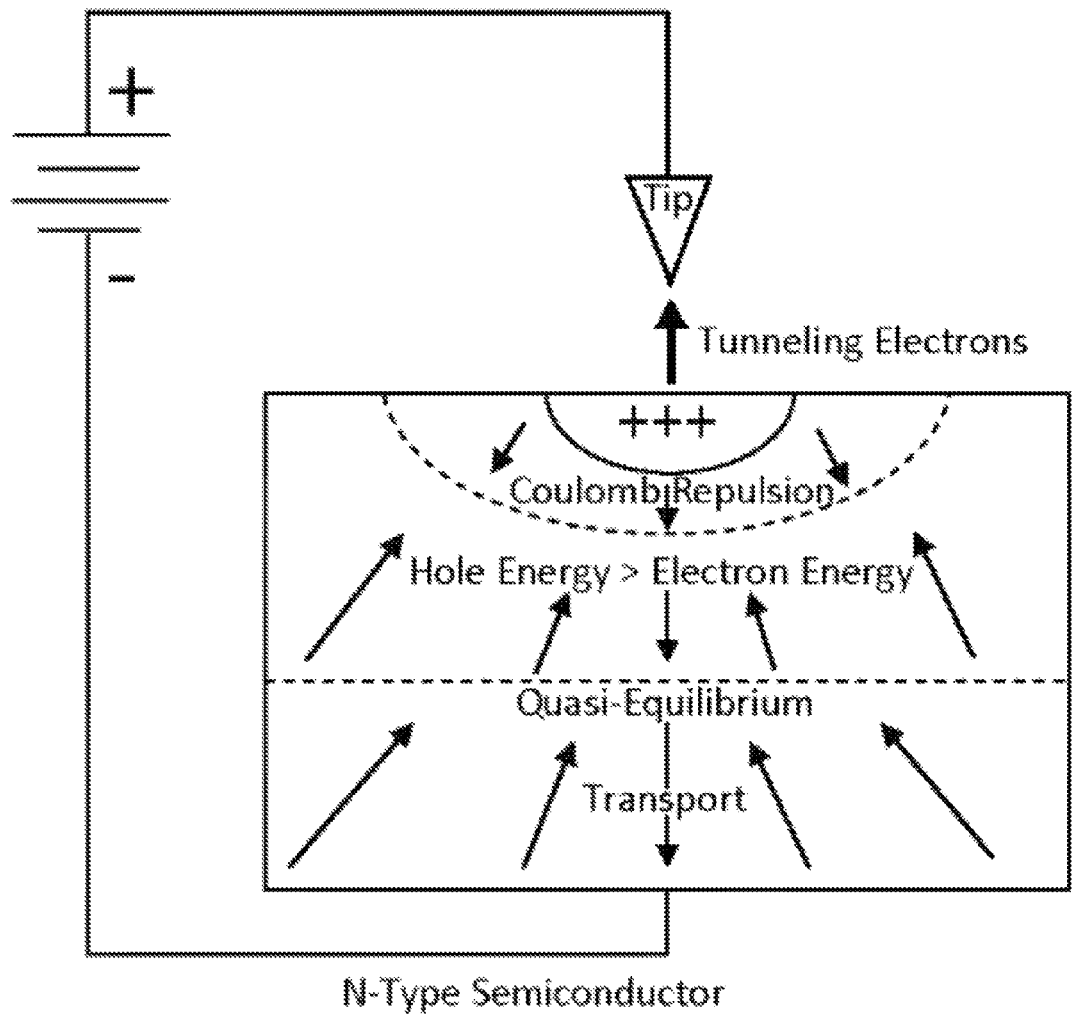
FIG. 5 is a block diagram depicting the creation of a Coulomb explosion within an n-type semiconductor sample.
Figure 6:
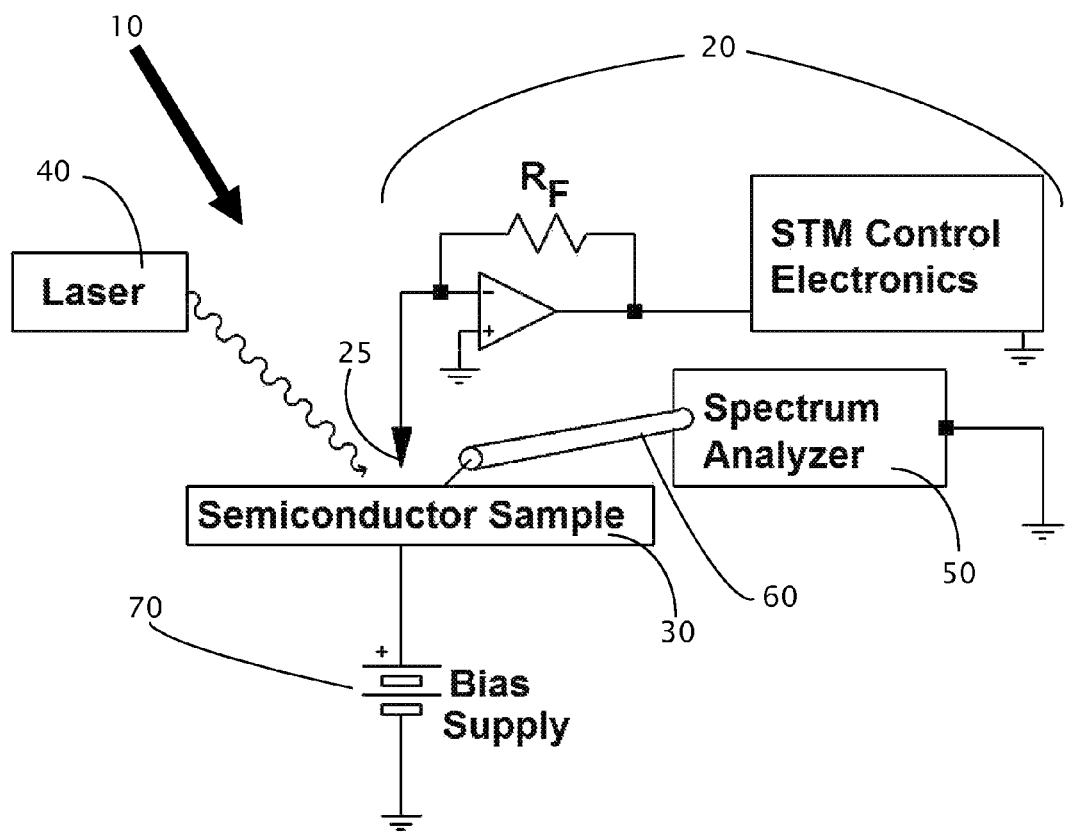
FIG. 6 is a block diagram of an apparatus used to measure the MFC with a semiconductor sample using a spreading resistance methodology, according to the present invention.
Figure 7:
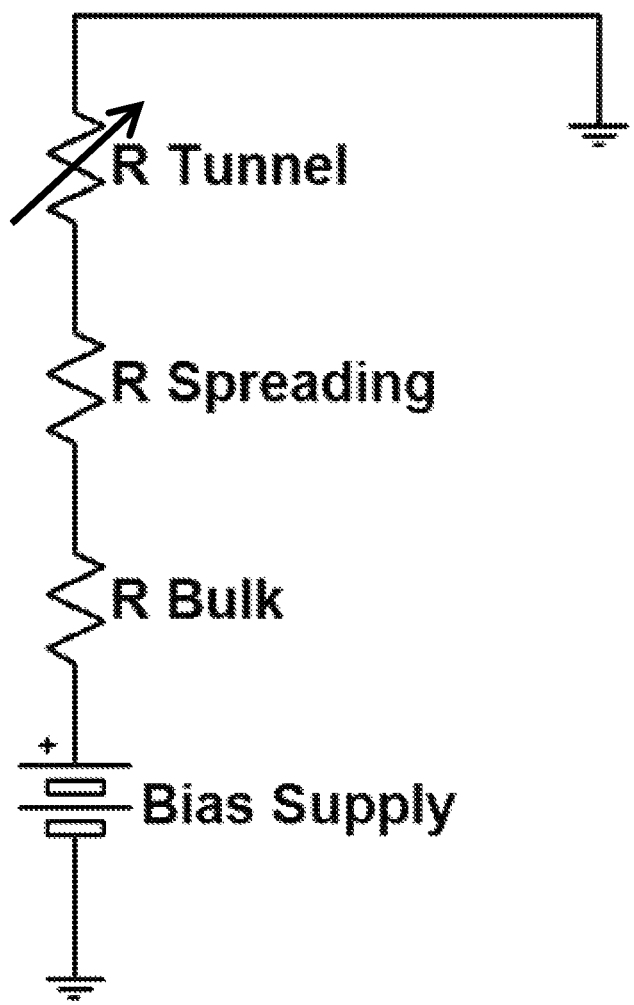
FIG. 7 is a circuit diagram depicting the DC equivalent circuit of the apparatus of FIG. 6.

As can be seen in FIG. 6, in one embodiment, an apparatus set-up 10 is a scanning tunneling microscope 20 positioned over a sample 30 onto which a mode-locked laser 40 is focused so that the laser emits a beam onto the tunneling junction between the STM 20 and the sample 30. The semiconductor sample 30 is forward biased 70, as is shown in FIG. 6 where a p-type semiconductor 30 is used and the voltage on the STM tip 25 is set to make the tip negative, thus allowing the carriers in the semiconductor sample to remain in the region directly beneath the tip. A spectrum analyzer 50 is connected into the circuit by means of a microwave probe 60 making contact with the sample 30 in close proximity to the tunneling junction. The microwave probe 60 may be formed of any suitably shielded conductor, such as coaxial cable. This probe should be insulated from the semiconductor to mitigate the effects of optical rectification. Such insulation will not affect the microwave frequency comb as the capacitance of the insulation will not attenuate the waveform. The dielectric layer of the insulation also acts as a DC block to prevent the flow of electrical charges between the semiconductor 30 and spectrum analyzer 50. As can be seen in the DC circuit diagram (FIG. 7), this circuit is essentially the same as in the prior art, except that instead of the resistance of the depletion region being represented, the spreading resistance ($R_{sp}$) is represented. The high frequency circuit (FIG. 8), however, replaces the resistance and capacitance of the depletion layer (represented as being in parallel with each other in FIG. 4) with a single spreading resistance.

Figure 8:
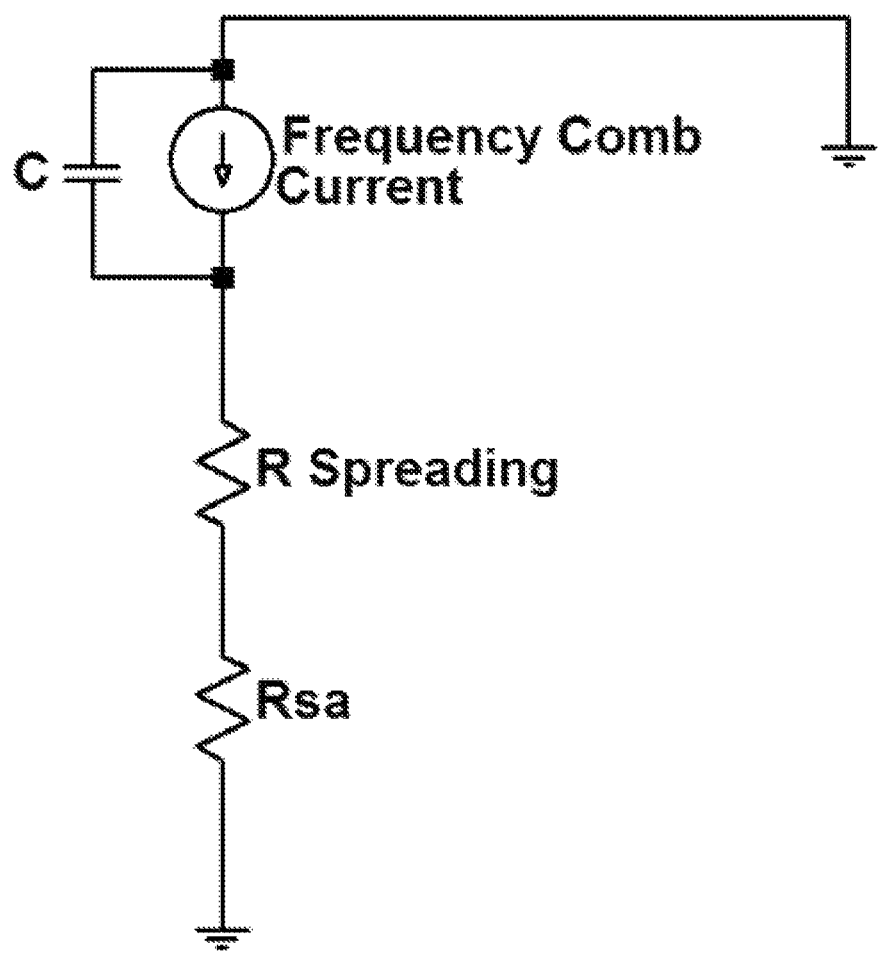
FIG. 8 is a circuit diagram depicting the high-frequency equivalent circuit of the apparatus of FIG. 6.

If the semiconductor is forward biased then there will be no depletion region, so the high frequency equivalent circuit in FIG. 8 yields a power described by the following equation:

$$P_n = \frac{R_{SA} I_{Sn} I_{Sn}^*}{2[1 + n^2 \omega_0^2 (R_{SA} + R_B + R_{SP})^2 C_S^2]} \quad (14)$$

where $I_{Sn}$ is the complex value of the current at the nth harmonic. The resistance of the semiconductor bulk ($R_B$) is negligible due to the proximity of the microwave probe 60 and the tunneling junction combined with the fact that the spreading resistance naturally dwarfs this value. The resistance of the spectrum analyzer ($R_{SA}$) is a known, constant, quantity and is easily accounted in the equation. Therefore, changes in power are readily attributed to the spreading resistance of the semiconductor sample. The spreading resistance from a hemispherical electrode with radius $R_0$ at the surface of a half-space of semiconductor having resistivity ρ is given by the following expression:

$$R_{SP} = \frac{\rho}{2\pi R_0} \quad (15)$$

Figure 9:
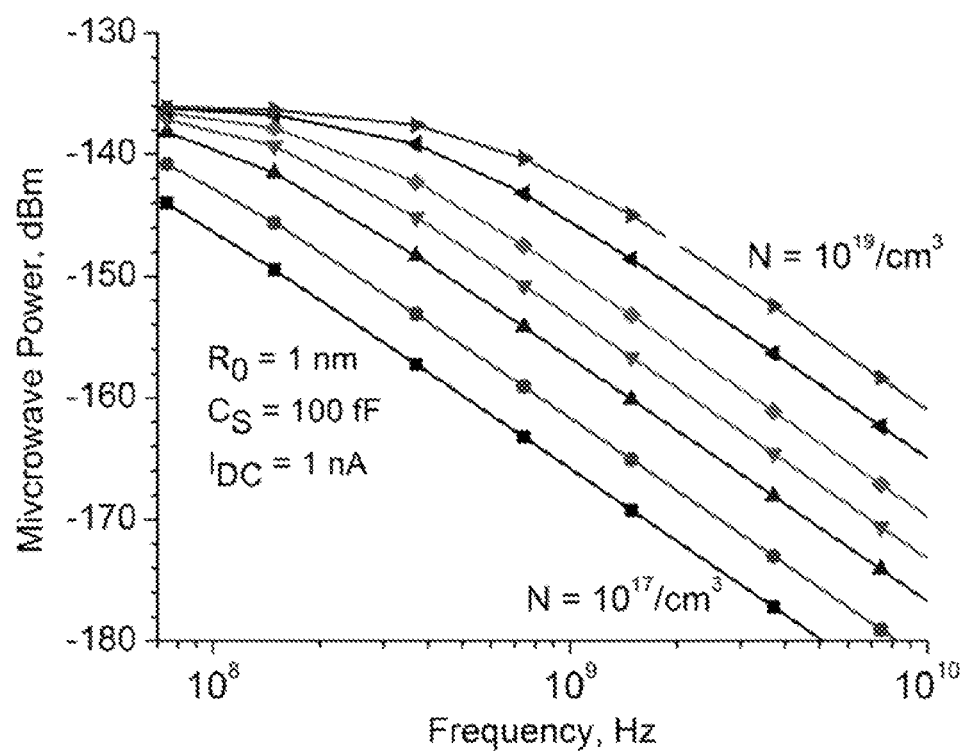
FIG. 9 is a graph depicting microwave power vs. frequency for different values of the carrier concentration N, using $R_O=1$ nm, $C_S=100$ fF, and $I_{DC}=1$ nA.
Figure 10:
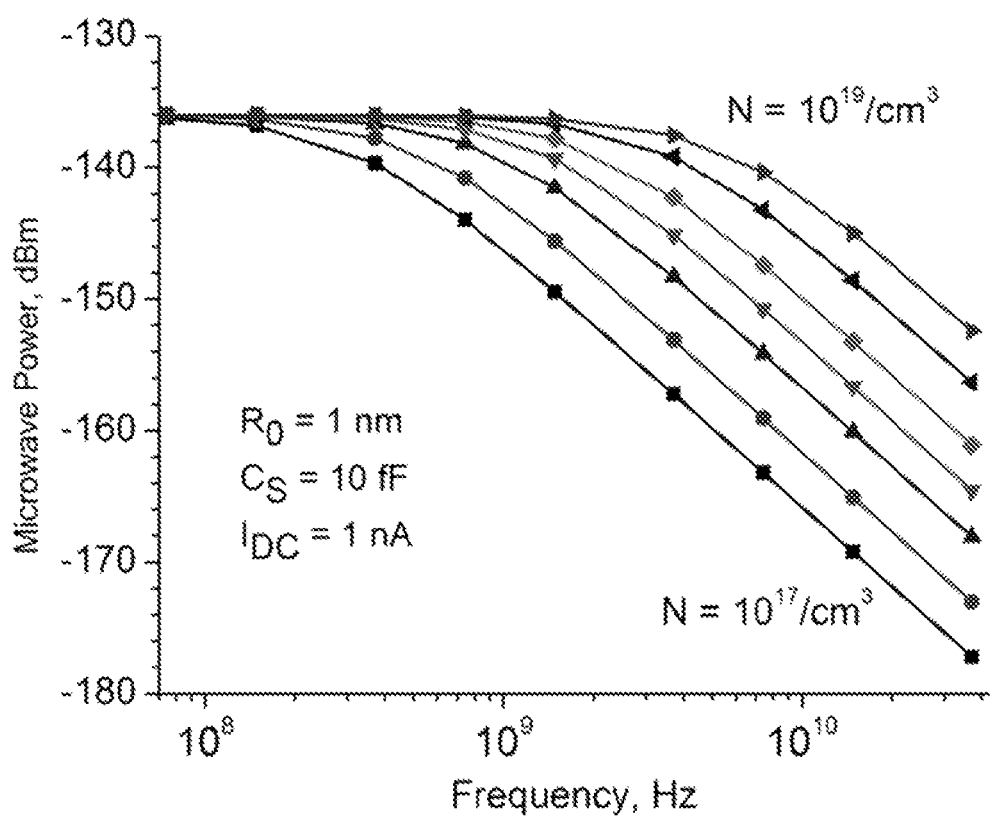
FIG. 10 is a graph depicting microwave power vs. frequency for different values of the carrier concentration N, using $R_O=1$ nm, $C_S=10$ fF, and $I_{DC}=1$ nA.
Figure 11:
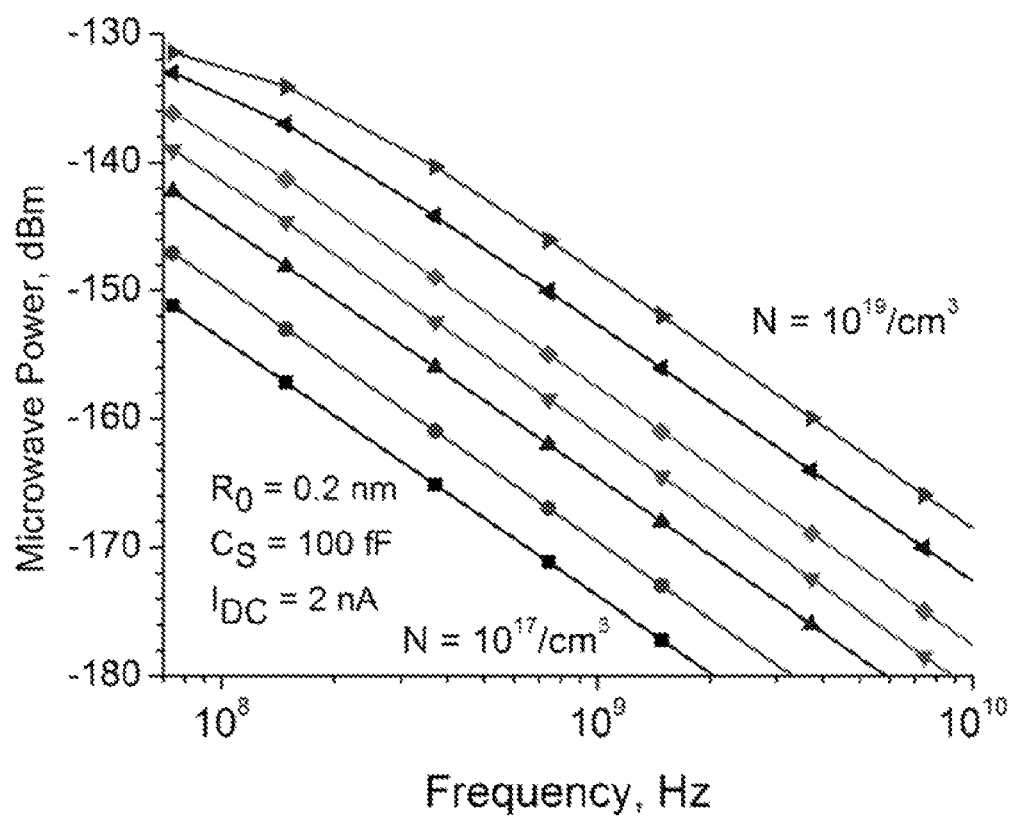
FIG. 11 is a graph depicting microwave power vs. frequency for different values of the carrier concentration N, using $R_O=0.2$ nm, $C_S=100$ fF, and $I_{DC}=2$ nA.

FIGS. 9-11, which were made using Eqs. (14) and (15), result from simulations allowing for spreading resistance in the semiconductor when there is no depletion. In each case a DC tunneling current $I_{DC}$ was specified to generate a constant current $I_{Sn}$ at the nth harmonic of the microwave frequency comb by optical rectification of the laser radiation within the tunneling junction. Different values of the shunt capacitance Cs were assumed, and the connection of the current in the MFC to the semiconductor was approximated by a hemisphere with radius $R_0$. The other parameters are $f_R$=74.254 MHz, $R_B$=100Ω, and $R_{SA}$=50Ω. In each of these three figures the curves are given for 7 different values of the density of carriers ("N") from $10^{17}$ to $10^{19}$/cm$^3$, in multiples of ×2, 5, 10, 20, 50, and 100.

FIG. 9 shows the microwave power that would be measured by the spectrum analyzer as a function of the frequency, with seven different values of the carrier density parameter N, $R_0$=1 nm, $C_S$=100 fF, and $I_{DC}$=1 nA. Note that changing the value of N causes a significant change in the microwave power. In fact, an increase in N by a factor of 2 causes the microwave power to increase 4 dB showing a gain so that the fractional increase in the microwave power exceeds the fractional increase in N. At the lower frequencies the response is less significant as shown in Eq. (14), but hyperspectral measurements may be made at many harmonics of the MFC, so that later it is possible to choose the harmonics at higher frequencies to mitigate this effect. The use of reasonable (low) values for the DC tunneling current reduces extraneous effects such as damage to the sample.

FIG. 10 is similar to FIG. 9, but the shunting capacitance is reduced by a factor of 10, from 100 fF to 10 fF. This change causes the current division due to the shunting capacitance to be less prominent at the lower frequencies which may be understood from Eq. (14). However, hyperspectral measurements may be made at many frequencies of the MFC, so that later it is possible to choose the harmonics at 10 times the frequencies which are shown in FIG. 11 to mitigate this effect. Another approach would be to use all of the hyperspectral data to obtain a best-fit of Eq. (14). However, in practice, it would be necessary to analyze the data using realistic numerical simulations, allowing for "atomistic" effects, but the simple analytical solutions in this report are made in order to show feasibility.

Dependence of the power in the MFC on the carrier density is dwarfed by other factors at lower frequencies. However, at much higher frequencies, measurements of the power are less accurate because of the higher signal to noise ratio. Depending upon the sample, dopant concentration, and shunting capacitance there is a zone of frequencies which are optimum for determining carrier concentration. This zone is readily determined by analyzing the data from many measured frequencies.

FIG. 11 shows the microwave power that would be measured by the spectrum analyzer as a function of the frequency, for seven different values of the carrier density N, with $R_0$=0.2 nm, $C_S$=100 fF, and $I_{DC}$=2 nA. This figure supports the feasibility of making measurements with sub-nm resolution because (1) The values of frequency and microwave power are comparable with those used in earlier measurements of the microwave frequency comb, and (2) the power measurements are sensitive to the value of the carrier concentration because it is seen that an increase in N by a factor of 2 causes the microwave power to increase 4 dB. As such, this improved method may be utilized to obtain measurements at resolutions finer than the present state of the art.

The carrier density is determined from the attenuation of the measured power in the MFC. This may be accomplished by calibrating the measured attenuation to control attenuation measured in at least one control semiconductor sample with a known carrier density. This corresponds to the procedure used in calibrating SSRM in which spreading resistance is compared to spreading resistance in known control samples.

Using the apparatus depicted in FIG. 6, the mode-locked, ultrafast laser 40 is directed to the tunneling junction between the tip 25 and the sample 30. A forward bias 70 (so that no depletion region is created) is applied to the junction and the laser 40 activated. This creates the microwave frequency comb. Hyperspectral measurements of the MFC, in particular its power, from which attenuation may be calculated, may be made in real time as the probe tip 25 (and, if necessary, the associated laser beam 40) is moved about the sample 30, or the sample 30 is moved relative to the probe tip 25, in a manner to seamlessly profile a specified area of the sample 30. The volume of semiconductor that is averaged in each measurement may be adjusted by raising or lowering the tip 25 (or sample 30), changing the effective spot size $R_0$ and thereby varying the radius of the measured region. Since the measured region may be less than 1 nm in size, SFCM may achieve sub-nanometer resolution. The power of the MFC at a given point on the sample 30 reveals the carrier density within the measured region and, as regions overlap, a three dimensional determination of carrier density may be inferred. By making hyperspectral measurements, the data for many harmonics of the MFC are taken in a single scan. Therefore, individual sets of harmonics may be chosen which are most suitable for determining carrier density without needing to repeat these measurements. In this manner, a three-dimensional model of carrier density may be determined in the sample, to a resolution of 1 nm or less, without destroying the sample.

In summary, a procedure is defined which is similar to SSRM—the present method of choice for sub-10 nm carrier profiling—but has the following unique features:

1. Unlike SSRM, SFCM is not a destructive method and, not being destructive, SFCM may take measurements seamlessly across a semiconductor sample.

2. There is a gain, in that a specific fractional change in the carrier concentration causes a larger fractional change in the measured microwave power, whereas SSRM has a gain of unity.

3. Hyperspectral measurements make it possible to record the data for a wide range of harmonics so that the best range may be chosen later during data reduction instead of having to repeat the measurements.

4. High-frequency effects which were not included in the present model of the semiconductor would cause the hyperspectral measurements to provide additional information about the electrical properties of the semiconductor. For example, ballistic transport introduces a series inductive reactance to the model and the dielectric function depends on the frequency.

5. The MFC sets the present state-of-the-art for narrow linewidth at microwave frequencies, which enables a high signal-to-noise ratio to improve the sensitivity and accuracy of the measurements. If it is necessary, the linewidth could be further reduced by stabilizing the pulse repetition frequency of the laser.

6. Instead of having fixed size probes as in SSRM, it is possible to vary the tip-sample separation in order to change the effective spot size $R_0$. Furthermore, varying the spot size enables determining the average value of the carrier concentration over different volumes to enable 3-D profiling.

7. In SSRM a fundamental limit of about 1 nm for the resolution is set by the values of Young's modulus and hardness for the tip, but with SFCM the resolution could be improved by stabilizing the separation of the tip relative to the sample, as well as the lateral scanning of the tip relative to the sample.

Although the present invention has been described with reference to preferred embodiments, numerous modifications and variations can be made and still the result will come within the scope of the invention. Such modifications and variations include the changing of polarity to account for forward biasing either type or p-type semiconductors. Other STM set-ups may be utilized to practice SFCM microscopy without departing from the spirit and scope of the invention, which is the actual use of the methodology. SFCM may be used to measure and determine other characteristics of a semiconductor sample. This can include reactance from the spreading impedance, and therefore the dielectric function of the sample, in addition to the spreading resistance measured in SSRM. Measurements of the amplitude and width of the current pulse as a function of distance from the tunneling junction may be used to determine carrier-carrier scattering. No limitation with respect to the specific embodiments disclosed herein is intended or should be inferred.

What is claimed is:

1. A method of measuring carrier density in a semiconductor sample, the method comprising:
   a. placing the semiconductor sample in a scanning tunneling microscope for analysis, said microscope having control electronics and a source for providing a bias voltage, a space between a tip electrode of said scanning tunneling microscope and the surface of the semiconductor sample being defined as a tunneling junction, an area directly beneath the tip electrode on the semiconductor sample through which charge carriers pass being defined as a spot;
   b. applying a forward bias voltage to the tunneling junction such that no depletion region is created in the semiconductor sample;
   c. projecting a pulsed output of a mode-locked laser onto the tunneling junction at a chosen repetition frequency in a manner to generate a microwave frequency comb with a fundamental frequency and a plurality of harmonic frequencies at integer multiples of a pulse repetition rate of the laser;
   d. measuring power output of the microwave frequency comb for at least one given frequency;
   e. determining attenuation of the power output of the microwave frequency comb due to spreading resistance of the semiconductor sample at the defined spot;
   f. calculating carrier density at the given spot from the attenuation.

2. The method of claim 1, further comprising moving the tip electrode and semiconductor sample relative to each other laterally in a manner to move the spot and thereby generate a carrier density map of the semiconductor sample.

3. The method of claim 2, further comprising varying a radius of the spot by varying a length of the tunneling junction such that carrier density may be determined to greater and lesser depths within the semiconductor sample, thereby generating a three-dimensional model of the carrier density within the semiconductor sample.

4. The method of claim 1, further comprising varying a radius of the spot by varying a length of the tunneling junction such that carrier density may be determined to greater and lesser depths within the semiconductor sample.

5. The method of claim 1, further comprising the steps of recording hyperspectral data regarding the power output at a set of harmonics of the microwave frequency comb, from which attenuation may be calculated.

6. The method of claim 1, wherein the step of determining the carrier density is accomplished by comparing the measured attenuation to a standard measured attenuation of at least one known semiconductor control sample with a known carrier concentration.

7. The method of claim 1, the spot having a radius no greater than 1 nm.

8. An apparatus for the practice of scanning frequency comb microscopy, the apparatus comprising:
   a. a scanning tunneling microscope, said scanning tunneling microscope further comprising control electronics, a microscope tip and a sample electrode;
   b. a means for providing a DC bias current;
   c. a laser; and
   d. a spectrum analyzer with a microwave probe tip;
   wherein a tunneling junction is defined as a length between said sample and the microscope tip and the probe tip is positioned proximate the tunneling junction while the laser projected onto an area of the sample about the tunneling junction while the means for providing a DC bias current provides a current to eliminate any depletion zones within the sample;
   wherein the laser is configured to project a mode-locked pulsed output onto the tunneling junction at a chosen repetition frequency in a manner to generate a microwave frequency comb with a fundamental frequency and a plurality of harmonic frequencies at integer multiples of a pulse repetition rate of the laser.

9. The apparatus of claim 8 further comprising the sample being selected from the set of samples consisting of n-type semiconductors and p-type semiconductors and a polarity of the means of providing a DC bias and a polarity of the microscope tip are selected such that no depletion zone occurs in the sample.

10. The apparatus of claim 8, the laser being mode locked.

11. The apparatus of claim 8, the microwave probe being insulated from the semiconductor.

12. The apparatus of claim 8, the microwave probe being positioned within 100 µm of the tunneling junction.

13. A method of measuring carrier density in a semiconductor sample, the method comprising:
   a. placing the semiconductor sample in a scanning tunneling microscope for analysis, said microscope having control electronics and a source for providing a bias voltage, a space between a tip electrode of said scanning tunneling microscope and the surface of the semiconductor sample being defined as a tunneling junction, an area directly beneath the tip electrode on the semiconductor sample through which charge carriers pass being defined as a spot;
   b. applying a forward bias voltage to the tunneling junction such that no depletion region is created in the semiconductor sample;
   c. projecting a pulsed output of a mode-locked laser onto the tunneling junction at a chosen repetition frequency in a manner to generate a microwave frequency comb with a fundamental frequency and a plurality of harmonic frequencies at integer multiples of a pulse repetition rate of the laser;
   d. measuring power output of the microwave frequency comb for at least one given frequency;
   e. calculating an inherent characteristic of the sample from the power output.

14. The method of claim 13, the inherent characteristic being selected from the set of inherent characteristics consisting of carrier-carrier scattering and reactive impedance.

* * * * *